United States Patent
Yang et al.

(10) Patent No.: US 10,548,538 B2
(45) Date of Patent: Feb. 4, 2020

(54) ELECTRONIC DEVICE AND ALARM CONTROL METHOD

(71) Applicants: BOE TECHNOLOGY GROUP CO., LTD., Beijing (CN); Fuzhou BOE Optoelectronics Technology Co., Ltd., Fujian (CN)

(72) Inventors: Chunmei Yang, Beijing (CN); Hui Chen, Beijing (CN); Qiaoni Wang, Beijing (CN); Xingming Chen, Beijing (CN); Zhijian Chen, Beijing (CN); Xin Xie, Beijing (CN); Ming Li, Beijing (CN); Xinyu Zhang, Beijing (CN)

(73) Assignees: BOE TECHNOLOGY GROUP CO., LTD., Beijing (CN); FUZHOU BOE OPTOELECTRONICS TECHNOLOGY CO., LTD., Fujian (CN)

( * ) Notice: Subject to any disclaimer, the term of this patent is extended or adjusted under 35 U.S.C. 154(b) by 0 days.

(21) Appl. No.: 16/161,133

(22) Filed: Oct. 16, 2018

(65) Prior Publication Data

US 2019/0274638 A1    Sep. 12, 2019

(30) Foreign Application Priority Data

Mar. 9, 2018    (CN) .......................... 2018 1 0194847

(51) Int. Cl.
G08B 1/08    (2006.01)
A61B 5/00    (2006.01)
(Continued)

(52) U.S. Cl.
CPC ............ *A61B 5/746* (2013.01); *A61B 5/0077* (2013.01); *A61B 5/0205* (2013.01);
(Continued)

(58) Field of Classification Search
CPC ..... A61B 5/746; A61B 5/0077; A61B 5/0205; A61B 5/1114; A61B 5/1172;
(Continued)

(56) References Cited

U.S. PATENT DOCUMENTS

| | | | |
|---|---|---|---|
| 2008/0214903 A1* | 9/2008 | Orbach | A61B 5/486 600/301 |
| 2017/0303864 A1* | 10/2017 | Su | A61B 5/742 |
| 2017/0310874 A1* | 10/2017 | Howard | H04N 5/23206 |

* cited by examiner

*Primary Examiner* — Phung Nguyen
(74) *Attorney, Agent, or Firm* — Calfee, Halter & Griswold LLP

(57) ABSTRACT

The present disclosure provides an electronic device and an alarm control method. The electronic device includes: a detecting component, configured to obtain a physiological feature parameter of a user; a first input component, configured to receive verification information inputted by the user; and a first processing component, configured to receive the inputted verification information via the first input component when determining that the physiological feature parameter obtained by the detecting component satisfies a presupposed condition, perform a normal operating mode of the electronic device when determining that the verification information is first preset verification information, and perform an alarm operation when determining that the verification information is second preset verification information. The alarm operation at least includes transmitting first prestored information to a first object.

18 Claims, 3 Drawing Sheets

(51) Int. Cl.
*A61B 5/1172* (2016.01)
*A61B 5/1171* (2016.01)
*G06K 9/00* (2006.01)
*A61B 5/11* (2006.01)
*A61B 5/0205* (2006.01)
*G08B 21/02* (2006.01)
*A61B 5/145* (2006.01)
*A61B 5/021* (2006.01)
*A61B 5/024* (2006.01)

(52) U.S. Cl.
CPC ............ *A61B 5/1114* (2013.01); *A61B 5/1172* (2013.01); *A61B 5/1176* (2013.01); *A61B 5/681* (2013.01); *A61B 5/748* (2013.01); *A61B 5/749* (2013.01); *G06K 9/00335* (2013.01); *G06K 9/00604* (2013.01); *G08B 21/02* (2013.01); *A61B 5/021* (2013.01); *A61B 5/024* (2013.01); *A61B 5/14532* (2013.01)

(58) Field of Classification Search
CPC ....... A61B 5/1176; A61B 5/681; A61B 5/748; A61B 5/749; G06K 9/00604; G08B 21/02
See application file for complete search history.

ELECTRONIC DEVICE AND ALARM CONTROL METHOD

CROSS-REFERENCE

This application is based upon and claims priority to Chinese Patent Application No. 201810194847.6, filed on Mar. 9, 2018, the entire contents thereof are incorporated herein by reference.

TECHNICAL FIELD

Embodiments of the present disclosure relate to an electronic device, and more particularly, to an electronic device and an alarm control method.

BACKGROUND

At present, people's material lives are improving faster and faster, and most people have increasingly demanding requirements for their own security. When people are in a dangerous state, it is a concern of the people how to tell others the dangerous state and ensure their own security. At present, performing an alarm operation by mobile phones is very convenient. However, when the alarm operation is performed through a communication device such as a mobile phone, it is needed to manually input information and set contacts, which may waste time and may likely make it impossible to perform the alarm operation due to restrictions of current environments. Therefore, performing the alarm operation by mobile phones is not convenient enough.

SUMMARY

The present disclosure provides an electronic device and an alarm control method thereof.

According to an aspect of the present disclosure, there is provided an electronic device includes:

a detecting component, configured to obtain a physiological feature parameter of a user;

a first input component, configured to receive verification information inputted by the user; and a first processing component, configured to receive the verification information via the first input component when determining that the physiological feature parameter obtained by the detecting component satisfies a presupposed condition, control the electronic device to perform a normal operating mode when the verification information received by the first input component is first preset verification information, and control the electronic device to perform an alarm operation when the verification information received by the first input component is second preset verification information; wherein the alarm operation at least comprises transmitting first prestored information to a first object.

In an embodiment of the present disclosure, the electronic device further includes a second input component. The second input component is configured to receive the verification information inputted by the user. The electronic device is configured to perform the normal operating mode when the verification information received by the second input component is third verification information. The first processing component is configured to turn off the second input component when determining that the physiological feature parameter obtained by the detecting component satisfies the presupposed condition.

In an embodiment of the present disclosure, the detecting component includes at least one of a heart rate sensing module, a blood pressure sensing module, and a blood glucose detecting component.

In an embodiment of the present disclosure, the electronic device further includes a first device and a second device in a mutual communication connection. The detecting component includes: a first detecting module arranged in the first device, and/or a second detecting module arranged in the second device. The first detecting module and the second detecting module are configured to obtain the physiological feature parameter of the user. The first input component includes: a first input module arranged in the first device, and/or a second input module arranged in the second device. The first processing component includes a first processing module arranged in the first device, and/or a second processing module arranged in the second device. The first processing module and the second processing module are configured to start the first input component when the physiological feature parameter obtained by the detecting component satisfies the presupposed condition. The first processing component is configured to control the electronic device to perform the normal operating mode when the verification information received by the first input component is first preset verification information, and perform the alarm operation when the verification information received by the first input component is second preset verification information.

In an embodiment of the present disclosure, the first device includes at least one of a mobile phone, a PAD, and a notebook computer; and the second device includes a wearable device, and the wearable device includes a smart wristband.

In an embodiment of the present disclosure, the first input component includes at least one of: a biological feature input module, a character input module, and a graphic input module. The second input component includes at least one of: a biological feature input module, a character input module, and a graphic input module. The biological feature input module includes at least one of a fingerprint input module, an iris input module, and a facial feature input module.

In an embodiment of the present disclosure, the first processing component is further configured to control the electronic device to perform the normal operating mode when performing the alarm operation or after performing the alarm operation.

In an embodiment of the present disclosure, the first processing component being configured to perform the alarm operation includes: performing a preset operation at a preset time interval, wherein the preset operation includes at least one of: photographing an image via a photographing device and storing the image, and transmitting the image to the first object; obtaining audio information via a voice recording device and storing the audio information, and transmitting the audio information to the first object; and obtaining positioning information via a positioning device and storing the positioning information, and transmitting the positioning information to the first object.

In an embodiment of the present disclosure, the first processing component is further configured to: query a monitoring apparatus within a preset range based on the obtained positioning information; store an identifier of the monitoring apparatus, and transmit the identifier to the first object; and the first processing component is further configured to obtain a corresponding monitoring video based on the queried monitoring apparatus.

In an embodiment of the present disclosure, the electronic device further includes a memory. The first processing component is configured to take the physiological feature parameter detected by the detecting component as a historical parameter and store the historical parameter into the memory in real time, and determine whether the detected physiological feature parameter satisfies the presupposed condition based on the historical parameter.

An embodiment of the present disclosure further provides an alarm control method, which is applied to the electronic device according to the above embodiments and includes: detecting a physiological feature parameter of a user; receiving inputted verification information via the first input component when determining that the physiological feature parameter satisfies the presupposed condition; and controlling the electronic device to perform the normal operating mode when the verification information is first preset verification information, and controlling the electronic device to perform the alarm operation when the verification information is second preset verification information; wherein the alarm operation at least comprises transmitting first pre-stored information to the first object.

In an embodiment of the present disclosure, the method further includes: turning off the second input component when the physiological feature parameter satisfies the presupposed condition; receiving the verification information via the second input component when the physiological feature parameter does not satisfy the presupposed condition; and controlling the electronic device to perform the normal operating mode when the verification information received by the second input component is third verification information.

In an embodiment of the present disclosure, the verification information includes at least one of: biological feature information, character information, and graphic information. The biological feature information includes at least one of fingerprint information, iris information, and facial feature information.

In an embodiment of the present disclosure, the method further includes: controlling the electronic device to perform the normal operating mode when performing the alarm operation or after performing the alarm operation.

In an embodiment of the present disclosure, the performing the alarm operation further includes: querying a monitoring apparatus within a preset range based on the obtained positioning information; and storing an identifier of the monitoring apparatus, and transmitting the identifier to the first object.

DETAILED DESCRIPTION

Figure 1:
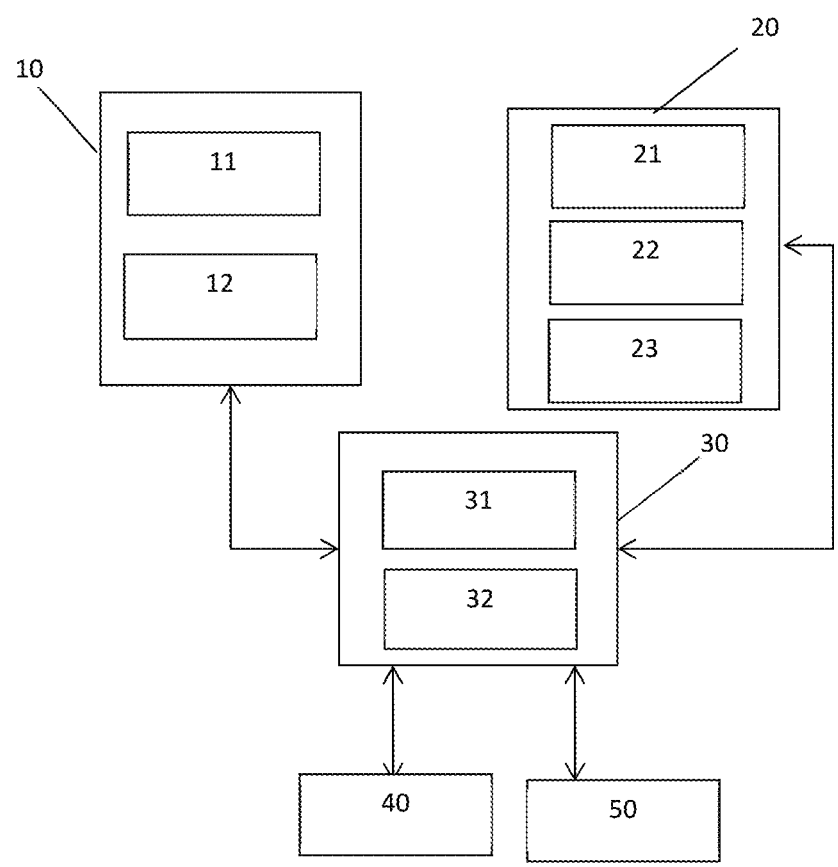
FIG. 1 is a schematic constructional diagram of an electronic device according to an embodiment of the present disclosure.

Specific embodiments of the present disclosure are described in detail below with reference to the accompanying drawings. However, such embodiments are not intended to be limiting of the present disclosure.

It should be understood that, various modifications can be made to the embodiments disclosed herein. Therefore the above description shall not be deemed as limitations but merely serves as examples of the embodiments. Other modifications can be obtained by those skilled in the art within the scope and spirit of the present disclosure.

The accompanying drawings, which are incorporated in and constitute a part of this specification, illustrate embodiments of the present disclosure and, together with the above general description of the present disclosure and the following detailed description of the embodiments, serve to explain the principles of the present disclosure.

Through the descriptions of preferred forms of non-limiting embodiments of the present disclosure hereinafter with reference to the accompanying drawings, these and other features of the present disclosure will become apparent.

It should be further understood that, though the present disclosure has been described with reference to some specific embodiments, those skilled in the art can implement various other equivalent embodiments comprising features described in the appended claims, all of which fall within the protection scope defined herein.

With reference to the accompanying drawings and the detailed descriptions, the above-described and other aspects, features, and advantages of the present disclosure will become more apparent.

The specific embodiments of the present disclosure are described hereinafter with reference to the accompanying drawings. However, it should be understood that the disclosed embodiments are only examples of the present disclosure, and may be implemented in various ways. The known and/or repeated functions and structures are not described in detail to avoid unnecessary or surplus details that obscure the present disclosure. Therefore, the specific structural or functional details of the present disclosure are not intended to be limiting, but are only used as the basis of the claims and representative basis for educating those skilled in the art to implement the present disclosure in various ways using any appropriate specific structures in essence.

In this specification, terms such as "in an embodiment", "in another embodiment", "in an additional embodiment", or "in other embodiments" may all refer to one or more the same or different embodiments of the present disclosure.

This embodiment of the present disclosure is described in detail below with reference to the accompanying drawings. This embodiment of the present disclosure provides an electronic device. The electronic device may obtain a physiological feature parameter of a user in real time, and enter an alarm mode of the electronic device when the physiological feature parameter is abnormal. At this moment, an alarm operation is performed when a password entered by the user is different from a password in a normal operating mode, and preconfigured information may be transmitted to a particular object to remind the object of current situations, thereby making it convenient to perform the alarm and improving security of the user.

As shown in FIG. 1, a schematic constructional diagram of an electronic device according to an embodiment of the present disclosure is illustrated. The electronic device in this embodiment of the present disclosure may include a detecting component 10, a first input component 20, a first processing component 30 respectively connecting to the detecting component 10 and the first input component 20, and a memory 40.

The electronic device in this embodiment of the present disclosure may be a portable device such as a mobile phone, a PAD or a portable notebook computer, etc. In an embodiment, the electronic device in this embodiment of the present disclosure may include a first device and a second device. The first device may include at least one of the mobile phone, the PAD, and the notebook computer. The second device may include a wearable device, and the wearable device includes a smart wristband or smart clothes, etc. A plurality of devices may be included in other embodiments, which are not described in detail.

The detecting component 10 in this embodiment of the present disclosure may obtain a physiological feature parameter of a user, for example, at least one of a blood pressure parameter, a heart rate parameter, and a blood glucose parameter. Specifically, the detecting component 10 may include at least one of a heart rate sensing module that can sense the user's heart rate, a blood pressure sensing module that can sense the user's blood pressure, and a blood glucose monitor that can detect the user's blood glucose concentration. The detecting component 10 may be arranged in one electronic device, or may be arranged in different electronic devices, and can establish data communications between different electronic devices.

For example, in the embodiment where the electronic device includes a first device and a second device, the detecting component may include a first detecting module 11 and/or a second detecting module 12. The first detecting module 11 may be arranged in the first device, the second detecting module 12 may be arranged in the second device, and the first device can perform data communications with the second device. Specifically, a wired or wireless communication module may be respectively arranged in the first device and the second device to establish the data communications between the two devices. The first detecting module 11 being arranged in the first device refers to the first detecting module 11 being arranged on a surface of the first device or in the first device. It may be used as a configuration of the embodiment of the present disclosure as long as the user's physiological feature parameter can be detected. The second detecting module 12 may be arranged in the second device configured as a wristband or smart clothes and so on, which may make it easy for the user to wear on one hand, and also can make it possible to detect corresponding physiological feature parameter on the other hand. The first detecting module 11 and the second detecting module 12 may be respectively configured as at least one of the blood pressure sensing module, the heart rate sensing module and the blood glucose detecting component. For example, the first detecting module 11 and the second detecting module 12 may be vibrational heart rate sensors, etc. Furthermore, the first detecting module and the second detecting module in this embodiment of the present disclosure may be the same type of detecting module or may be different types of detecting modules. For example, both the first detecting module and the second detecting module may be heart rate sensing modules, or the first detection module may be the blood pressure sensing module, and the second detecting module may be the blood glucose detecting component. Different configurations may be made in different embodiments to improve applicability and user experience.

Moreover, the first input component 20 may be configured to receive verification information inputted by the user. The verification information may include at least one of biological feature information, character information, and gesture information. For example, the first input component 20 may include: a biological feature input module 21, a character input module 22, and a graphic input module 23. The biological feature input module 21 may be configured to obtain the user's biological feature information. For example, the biological feature input module 21 may include at least one of a fingerprint input module configured to obtain the user's fingerprint information, an iris input module configured to obtain the user's iris information, a voice-print input module configured to recognize the user's voice-print information, and a facial feature input module configured to recognize the user's facial feature. The character input module 22 is configured to receive digits, letters or other symbol composition character information inputted by the user. The graphic input module 23 may receive graphic gesture information inputted by the user. The user may set the verification information in different ways according to habits and execute control of the electronic device by using the verification information as a password.

In this embodiment of the present disclosure, when the electronic device includes the first device and the second device, the first input component 20 also may include a first input module and/or a second input module. The first input module is arranged in the first device, the second input module is arranged in the second device. The first input module and the second input module may be respectively configured to receive the verification information inputted by the user, and transmit the verification information to the processing component. Likewise, the first input module and the second input module in this embodiment of the present disclosure may be the same type of input module or may be different types of input modules.

The first processing component 30 may be respectively connected to the detecting component 10 and the first input component 20, and may receive the inputted verification information via the first input component 20 when determining that the physiological feature parameter obtained by the detecting component 10 satisfies a presupposed condition, control the electronic device to perform a normal operating mode when the verification information is first verification information, and control the electronic device to perform an alarm operation when the verification information is second verification information. The alarm operation at least includes transmitting first prestored information to a first object. In an embodiment, the first processing component 30 may start the first input component 20 when the physiological feature parameter obtained by the detecting component 10 satisfies the presupposed condition, such that the first input component executes the operation of receiving the verification information. That is, it may be implemented a fact that the first input component is not started until the first input component needs to execute the operation.

Likewise, the first processing component 30 also may include a first processing module 31 arranged in the first device, and/or a second processing module 32 arranged in the second device. The first processing module 31 and the second processing module 32 may execute all functions of the first processing component 30.

Moreover, in this embodiment of the present disclosure, the electronic device may further include a second input component 50, which also may be configured to receive the verification information inputted by the user. Furthermore, the first processing component 30 may turn off the second input component 50 when determining that the physiological feature parameter obtained by the detecting component 10 satisfies the presupposed condition. That is, an alarm mode may be executed when the user's physiological feature parameter satisfies the presupposed condition. At this moment, the first input component 20 may be turned on, and the second input component 50 may be turned off. In the meanwhile, when the user's physiological feature parameter does not satisfy the presupposed condition, the second input component 50 may be turned on, and the first input component 20 may be turned off.

In this embodiment of the present disclosure, in the state when the second input component 50 is turned on, the electronic device may perform the normal operating mode of the electronic device based on the received third verification information. At this moment, the first processing component 30 may verify the verification information received by the second input component 50, and may perform the normal operating mode of the electronic device when the verification information is the third verification information. In other embodiments, the electronic device may further include a second processing component. The second processing component may receive the physiological feature parameter detected by the detecting component, may turn off the second input component 50 when the physiological feature parameter satisfies the presupposed condition, may turn on the second input component 50 when the physiological feature parameter does not satisfy the presupposed condition, and may perform the normal operating mode of the electronic device when the verification information received by the second input component 50 is the third verification information. In this embodiment of the present disclosure, the second processing component and the first processing component may be configured in one processing device, or may be configured as different processing devices. Furthermore, the first verification information and the third verification information may be the same verification information or may be different verification information. Moreover, in this embodiment of the present disclosure, the verification information received by the second input component 50 may include at least one of biological feature information, character information, and gesture information. For example, the second input component also may include: a biological feature input module, a character input module, and a graphic input module. The biological feature input module 1 may be configured to obtain the user's biological feature information. For example, the biological feature input module may include at least one of a fingerprint input module configured to obtain the user's fingerprint information, an iris input module configured to obtain the user's iris information, a voiceprint input module configured to recognize the user's voiceprint information, and a facial feature input module configured to recognize the user's facial feature. The character input module is configured to receive digits, letters or other symbol composition character information inputted by the user. The graphic input module 23 may receive graphic gesture information inputted by the user. The user may set the verification information in different ways according to habits and execute control of the electronic device by using the verification information as a password. The first input component and the second input component may be the same input component or may be different input components.

Furthermore, in this embodiment of the present disclosure, the electronic device may be preconfigured with a first object and first information corresponding to the first object. The preconfigured first object includes a name and a communication address of the first object. The communication address may include a telephone number, an E-mail address, and an IP address, etc. The first information may be transmitted to the first object based on the communication address when the alarm operation is performed. Moreover, the first information may be content information preedited by the user or video information or audio information prerecorded by the user. The first information may be transmitted to the first object when the alarm operation is performed. The first object and the first information may be stored in a memory 40 of the electronic device or may be directly stored in the first processing component 30. The first processing component 30 may read the above information from the memory 40 to perform the corresponding operation. The memory 40 may be arranged inside the electronic device or may be arranged outside the electronic device as long as the electronic device can establish a data connection with the memory, which may fall within the scope of protection of the embodiment of the present disclosure.

Specifically, the first processing component 30 may receive the physiological feature parameter obtained from the detecting component 10, and may enter the alarm mode when an exception occurs in the physiological feature parameter (the presupposed condition is satisfied). The physiological feature parameter satisfying the presupposed condition includes: the obtained physiological feature parameter falls outside a preset standard range, correspondingly, different physiological features have different preset standard ranges, and different users may have different preset standard ranges. The preset standard range may be a range value generated based on information captured in the user's daily life, or may be a standard range value inputted by the user.

Moreover, the electronic device uses a double password separation system to perform a security control operation. That is, at least two types of preset verification information may be included. For example, the verification information may include first verification information and second verification information. When the user inputs the first verification information, the first processing component 30 may perform the normal operating mode of the electronic device based on the first verification information, for example, entering a corresponding program page such as a main interface of device. When the user inputs the second verification information, the first processing component 30 may perform the alarm operation of the electronic device, i.e., the preconfigured first information may be transmitted to the first object. At this moment, the first processing component 30 also may display prompt information on the electronic device. The prompt information may be, for example, information prompting a password input error. In an embodiment, just like the first verification information, the first processing component 30 may enter the corresponding program interface of device to perform the normal operation of the electronic device. Through the above configuration, the alarm operation may be performed in unobservable cases, and thus the user security may be improved.

Figure 2:
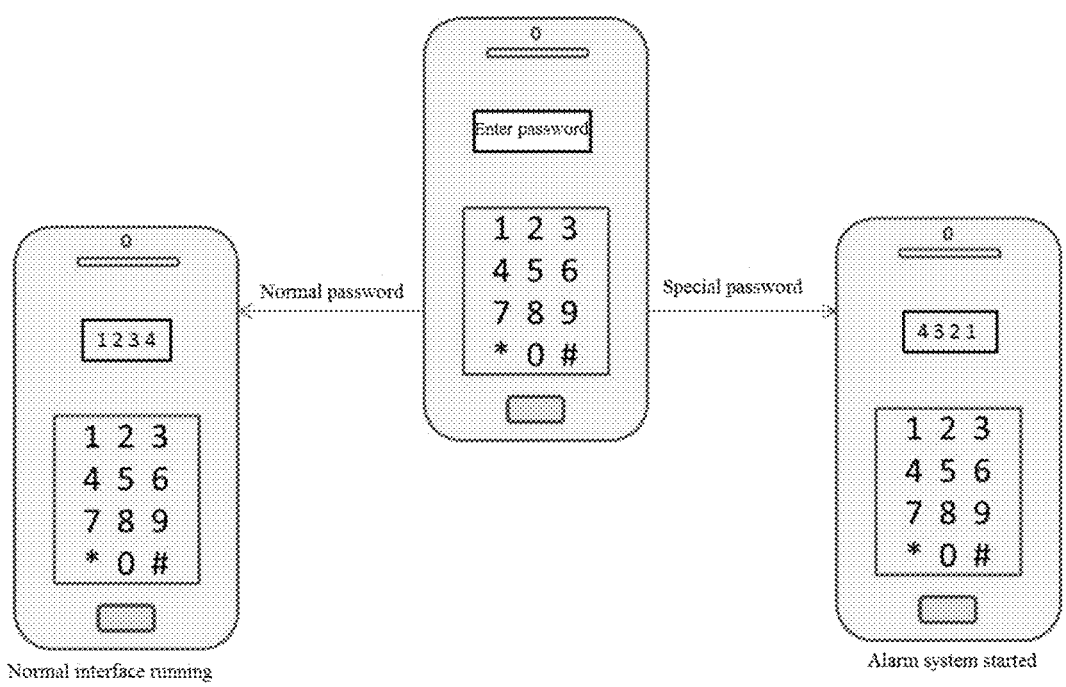
FIG. 2 is a schematic diagram when first verification information and second verification information are the same type of verification information according to an embodiment of the present disclosure.

Moreover, the first verification information and second verification information in this embodiment of the present disclosure may be the same type of verification information or may be different types of verification information. As shown in FIG. 2, a schematic diagram when the first verification information and the second verification information in this embodiment of the present disclosure are the same type of verification information is shown. The first verification information and the second verification information may be composed of characters. For example, the first verification information is 1234, and the second verification information is 4321. The user may input the second verification information when the alarm operation is performed. In other embodiments of the present disclosure, the first verification information and the second verification information also may be audio verification information, graphic verification information, biological feature information and so on, which are not specified here.

In another embodiment of the present disclosure, the first verification information and the second verification information may be different types of verification information. For example, the first verification information may be fingerprint information, and the second verification information may be character information. In other embodiments, the first verification information and the second verification information respectively may be two types of character verification information, biological feature information, audio information, or other verification information. The processing component 30 also may be further configured to turn off the biological feature input module 21 of the input component 20 when the physiological feature parameter received from the detecting component 10 satisfies the presupposed condition, wherein the second verification information is composed of characters or graphs. In an embodiment, the processing component 30 also may be configured to turn off the character input module or the graphic input module when the physiological feature parameter satisfies the presupposed condition. At this moment, the second verification information includes preset biological feature information. That is, when the alarm operation is performed, the first processing component 30 may turn off the input module except the input module of the second verification information, such that the user may input the verification information only by means of the input module corresponding to the second verification information to perform the alarm operation. This configuration may further ensure that the user can input the verification information required to perform the alarm operation, and failure of performing the alarm operation due to misinput of other verification information may be prevented, and thus accuracy of alarm may be further enhanced.

For example, when the first verification information is the fingerprint information, the fingerprint unlocking function may be automatically disenabled in case of abnormal heart rhythm to prevent from entering the normal operating mode due to direct fingerprint unlocking. In this case, the user may select to input a corresponding password based on current environment so as to avoid interference caused by other emotional excitements, thereby preventing the device from making an erroneous determination, and improving alarm accuracy. A double password separation mode is automatically enabled when the heart rate is abnormal if no normal password is set, and the user may perform the operation according to circumstances.

Furthermore, according to the above embodiment, the first processing component 30 also may take the physiological feature parameter detected by the detecting component 10 as a historical parameter and store the historical parameter into the memory 40 in real time, and determine whether the detected physiological feature parameter satisfies the presupposed condition based on the historical parameter. The user's standard physiological feature parameter range in normal circumstances may be generated based on the user's daily physiological feature parameter, and this range is used as a reference to determine whether the physiological feature parameter obtained by the detecting component 10 satisfies the presupposed condition. That is, it is determined whether the physiological feature parameter falls outside the above standard physiological feature parameter range. It is determined that the physiological feature parameter satisfies the presupposed condition if the physiological feature parameter falls outside the standard physiological feature parameter range, otherwise it is determined that the physiological feature parameter does not satisfy the presupposed condition.

For example, if the electronic device is robbed, the detecting component 10 in the electronic device may detect that the user's heart rate is abnormal in the robbery, or even detect heart rates of two persons. At this moment, the electronic device may automatically perform the alarm operation. When one of the first device and the second device is robbed, the other device may perform detection of the user's physiological feature parameter, such that the other device may perform an alarm based on the received second verification information when the physiological feature parameter is abnormal. in an embodiment, when one of the first device and the second device is robbed, the detecting component in the robbed device may detect the robber's physiological feature parameter, and may perform the alarm operation or may perform the alarm operation by means of the second device when determining that this parameter does not conform to the user's standard physiological feature parameter or that it is a physiological feature parameter of a second user other than a preset user.

In an embodiment, when a wearable component such as a smart wristband is robbed, the user's heart rate is abnormal, and the wristband may sense an external force and thus automatically turn on the alarm system. At this moment, the wearable component also may communicate with the electronic device and perform the alarm operation by means of the electronic device.

The alarm operation in this embodiment of the present disclosure is described below in detail. In addition to transmitting the preconfigured first information to the first object, the first processing component 30 also may perform a preset operation at a preset time interval, wherein the preset operation includes at least one of:

photographing an image via a photographing device and storing the image, and transmitting the image to the first object;

obtaining audio information via a voice recording device and storing the audio information, and transmitting the audio information to the first object; and obtaining positioning information via a positioning device and storing the positioning information, and transmitting the positioning information to the first object.

That is, the first processing component 30 also may connect to at least one of a photographing device, a recording device and a positioning device of the electronic device, and may store image information obtained by the photographing device, audio information obtained by the recording device or positioning information obtained by the positioning device into the memory, and transmit the obtained information to the first object, such that the first object may learn about the user's current situations and accordingly adopt effective safety precautions.

For example, when the user is coerced to call the user's relatives, because of abnormal heart rate caused by emotional variations, the detecting component 10 may detect that the user's current heart rate parameter satisfies the presupposed condition and enter the alarm mode. At this moment, the user inputs a special password, i.e., the second verification information to start the alarm system. At this moment, the electronic device automatically takes photos and records voices at background, and keeps on transmitting the photos, the recorded voices and the current position, and preset information or voices (for example, I am in danger, please help me) to the designated first object.

Further, in this embodiment of the present disclosure, when the detecting component 10 detects that the physiological feature parameter is a second object, the first processing component 30 may transmit the physiological feature parameter of the second object to the first object. The physiological feature parameter of the second object is different from the physiological feature parameter inputted by the user in advance. For example, when the user runs into a robbery or loses at least one of the electronic device and the wearable component, the detecting component 10 may detect fingerprint information of the robber when the robber uses the electronic device, and the first processing component 30 performs the alarm operation when determining that the fingerprint information is not the fingerprint verification information inputted by the user in advance. The robber's fingerprint information may be transmitted to the preconfigured first object to assist the user or the police in obtaining the robber's identity information.

In another embodiment, the first processing component 30 also may search for a monitoring apparatus within a preset range based on positioning information obtained by the positioning device, store an identifier of the monitoring apparatus, and transmit the identifier to the first object.

For example, the electronic device may establish a communication connection with an external server to request to obtain the monitoring apparatus within the preset range of the positioning information. Specifically, the first processing component 30 may transmit a first request to the server based on the received second verification information, wherein the first request may include the positioning information obtained by the positioning device. When the server receives the first request, the server may obtain the identifier of the monitoring apparatus within a preset range from the positioning information in the first request, and return the obtained identifier back to the electronic device. The first processing component 30 may store the identifier of the monitoring apparatus returned by the server into the memory, and transmit the identifier of the monitoring apparatus within the preset range to the first object. In this way, the user's security is further improved, and the alarm operation may be performed based on a monitoring video obtained by the monitoring apparatus. In an embodiment, the first processing component 30 also may obtain the corresponding monitoring video based on the monitoring apparatus searched out.

In an embodiment, configuration information of the monitoring apparatus may be stored in the memory of the electronic device. The configuration information may include, for example, location information and corresponding identification information of the monitoring apparatus within a certain regional range. After obtaining the second verification information, the first processing component may search the identifier of the monitoring apparatus within the preset range based on the positioning information obtained by the positioning device, and transmit the identifier to the first object.

Through the above configuration, information on the monitoring apparatus within the preset range may be conveniently obtained, which may conveniently help the user to obtain the corresponding monitoring video and further guarantee security of the user and collection of evidence, etc.

Furthermore, in another embodiment of the present disclosure, when the first device establishes a communication connection with the wearable component used as the second device, wherein the wearable component may include, for example, a smart wristband, smart clothes or the like, the wearable component also may be provided with the detecting component 10. The first processing component 30 also may include a first processing module 31 and a second processing module 32, wherein the first processing module 31 and the second processing module 32 may execute the same configuration as the first processing component 30, such that no matter the first device or the wearable component in communication connection with the first device may perform control of the alarm operation. When one of the electronic device and the wearable component goes wrong or the alarm operation cannot be performed due to restriction of other conditions, the other one may perform the alarm operation, and thus availability of the alarm operation may be further improved.

Here, the first device and the second device may perform data transmission by way of wireless communication connection. The first device and the second device may respectively include a wireless communication module such as a Bluetooth module, a WiFi module, or a near field communication (NFC) module.

Furthermore, the first input component 20 also may receive second information, and the first processing component 30 may stop performing the alarm operation based on the second information. The first input component 20 may receive the second information by receiving preset voice information, preset key information or preset gesture operation information, etc.

In conclusion, the electronic device in this embodiment of the present disclosure may conveniently and safely perform the preset alarm operation and can guarantee security of the user.

Figure 3:
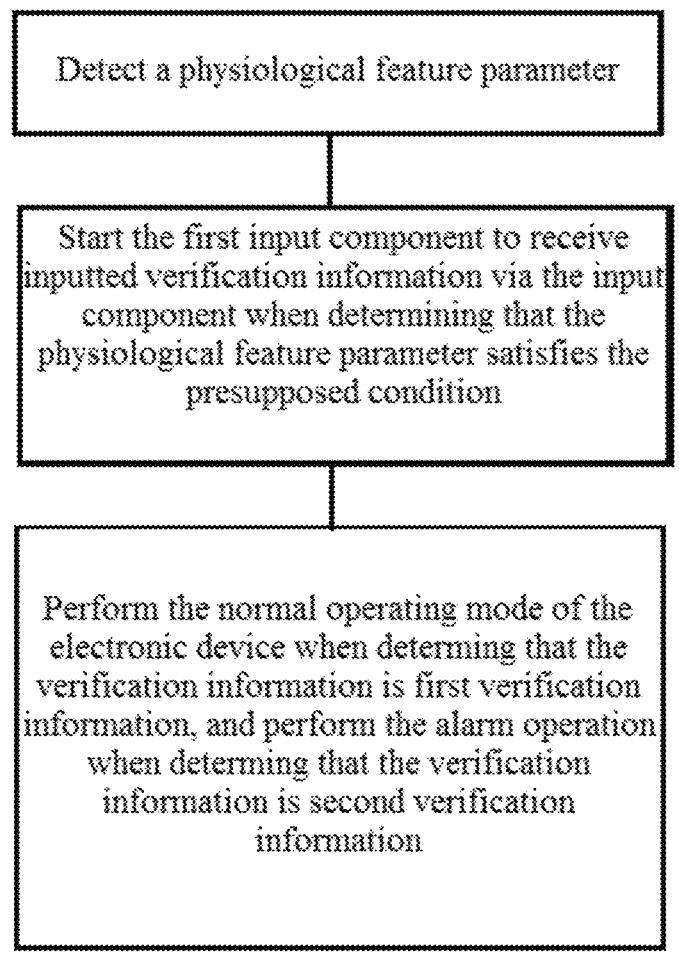
FIG. 3 is a schematic flowchart of an alarm control method according to an embodiment of the present disclosure.

Moreover, an embodiment of the present disclosure further provides an alarm control method, which may be applied to the electronic device according to the above embodiment. As shown in FIG. 3, a schematic flowchart of the alarm control method according to this embodiment of the present disclosure is shown.

The alarm control method in this embodiment of the present disclosure may include:

detecting a physiological feature parameter of a user;

receiving inputted verification information via the first input component when determining that the physiological feature parameter satisfies the presupposed condition; and performing the normal operating mode of the electronic device when the verification information is first preset verification information, and controlling the electronic device to perform the alarm operation when determining that the verification information is second preset verification information.

The alarm operation at least includes transmitting first prestored information to the first object.

The electronic device in this embodiment of the present disclosure may be a portable device such as a mobile phone, a PAD or a portable notebook computer, etc. In an embodiment, the electronic device in this embodiment of the present disclosure may include a first device and a second device. The first device may include at least one of the mobile phone, the PAD, and the notebook computer. The second device may include a wearable device, and the wearable device includes a smart wristband or smart clothes, etc. A plurality of devices may be included in other embodiments, which are not described in detail.

The detecting component 10 in this embodiment of the present disclosure may obtain a physiological feature parameter of a user, for example, at least one of a blood pressure parameter, a heart rate parameter, and a blood glucose parameter. Specifically, the detecting component 10 may include at least one of a heart rate sensing module that can sense the user's heart rate, a blood pressure sensing module that can sense the user's blood pressure, and a blood glucose monitor that can detect the user's blood glucose concentration. The detecting component 10 may be arranged in one electronic device, or may be arranged in different electronic devices, and can establish data communications between different electronic devices.

For example, in the embodiment where the electronic device includes a first device and a second device, the detecting component may include a first detecting module 11 and/or a second detecting module 12. The first detecting module 11 may be arranged in the first device, the second detecting module 12 may be arranged in the second device, and the first device can perform data communications with the second device. Specifically, a wired or wireless communication module may be respectively arranged in the first device and the second device to establish the data communications between the two devices. The first detecting module 11 being arranged in the first device refers to the first detecting module 11 being arranged on a surface of the first device or in the first device. It may be used as a configuration of the embodiment of the present disclosure as long as the user's physiological feature parameter can be detected. The second detecting module 12 may be arranged in the second device configured as a wristband or smart clothes and so on, which may make it easy for the user to wear on one hand, and also can make it possible to detect corresponding physiological feature parameter on the other hand. The first detecting module 11 and the second detecting module 12 may be respectively configured as at least one of the blood pressure sensing module, the heart rate sensing module and the blood glucose detecting component. For example, the first detecting module 11 and the second detecting module 12 may be vibrational heart rate sensors, etc. Furthermore, the first detecting module and the second detecting module in this embodiment of the present disclosure may be the same type of detecting module or may be different types of detecting modules. For example, both the first detecting module and the second detecting module may be heart rate sensing modules, or the first detection module may be the blood pressure sensing module, and the second detecting module may be the blood glucose detecting module. Different configurations may be made in different embodiments to improve applicability and user experience.

Moreover, the first input component 20 may be configured to receive verification information inputted by the user. The verification information may include at least one of biological feature information, character information, and gesture information. For example, the first input component 20 may include: a biological feature input module 21, a character input module 22, and a graphic input module 23. The biological feature input module 21 may be configured to obtain the user's biological feature information. For example, the biological feature input module 21 may include at least one of a fingerprint input module configured to obtain the user's fingerprint information, an iris input module configured to obtain the user's iris information, a voiceprint input module configured to recognize the user's voiceprint information, and a facial feature input module configured to recognize the user's facial feature. The character input module 22 is configured to receive digits, letters or other symbol composition character information inputted by the user. The graphic input module 23 may receive graphic gesture information inputted by the user. The user may set the verification information in different ways according to habits and execute control of the electronic device by using the verification information as a password.

In this embodiment of the present disclosure, when the electronic device includes the first device and the second device, the first input component also may include a first input module and/or a second input module. The first input module is arranged in the first device, the second input module is arranged in the second device. The first input module and the second input module may be respectively configured to receive the verification information inputted by the user, and transmit the verification information to the processing component. Likewise, the first input module and the second input module in this embodiment of the present disclosure may be the same type of input module or may be different types of input modules.

The first processing component 30 may be respectively connected to the detecting component 10 and the first input component 20, and may receive the inputted verification information via the first input component 20 when determining that the physiological feature parameter obtained by the detecting component 10 satisfies a presupposed condition, perform a normal operating mode of the electronic device when the verification information is first verification information, and control the electronic device to perform an alarm operation when the verification information is second verification information. The alarm operation at least includes transmitting first prestored information to a first object. Likewise, the first processing component 30 also may include a first processing module 31 arranged in the first device, and/or a second processing module 32 arranged in the second device. The first processing module 31 and the second processing module 32 may execute all configurations of the first processing component 30.

Moreover, in this embodiment of the present disclosure, the electronic device may further include a second input component 50, which also may be configured to receive the verification information inputted by the user. The first processing component 30 is configured to turn off the second input component 50 when determining that the physiological feature parameter obtained by the detecting component 10 satisfies the presupposed condition. That is, an alarm mode may be executed when the user's physiological feature parameter satisfies the presupposed condition. At this moment, the first input component 20 may be turned on, and the second input component 50 may be turned off. In the meanwhile, when the user's physiological feature parameter does not satisfy the presupposed condition, the second input component 50 may be turned on, and the first input component 20 may be turned off.

In this embodiment of the present disclosure, in the state when the second input component 50 is turned on, the electronic device may perform the normal operating mode of the electronic device based on the received third verification information. At this moment, the first processing component 30 may verify the verification information received by the second input component 50, and may perform the normal operating mode of the electronic device when the verification information is the third verification information. In other embodiments, the electronic device may further include a second processing component. The second processing component may receive the physiological feature parameter detected by the detecting component, may turn off the second input component 50 when the physiological feature parameter satisfies the presupposed condition, may turn on the second input component 50 when the physiological feature parameter does not satisfy the presupposed condition, and may perform the normal operating mode of the electronic device when the verification information received by the second input component 50 is the third verification information. In this embodiment of the present disclosure, the second processing component and the first processing component may be configured in one processing device, or may be configured as different processing devices. Furthermore, the first verification information and the third verification information may be the same verification information or may be different verification information. Moreover, in this embodiment of the present disclosure, the verification information received by the second input component 50 may include at least one of biological feature information, character information, and gesture information. For example, the second input component also may include: a biological feature input module, a character input module, and a graphic input module. The biological feature input module 1 may be configured to obtain the user's biological feature information. For example, the biological feature input module may include at least one of a fingerprint input module configured to obtain the user's fingerprint information, an iris input module configured to obtain the user's iris information, a voiceprint input module configured to recognize the user's voiceprint information, and a facial feature input module configured to recognize the user's facial feature. The character input module is configured to receive digits, letters or other symbol composition character information inputted by the user. The graphic input module 23 may receive graphic gesture information inputted by the user. The user may set the verification information in different ways according to habits and execute control of the electronic device by using the verification information as a password. The first input component and the second input component may be the same input component or may be different input components.

Furthermore, in this embodiment of the present disclosure, the electronic device may be preconfigured with a first object and first information corresponding to the first object. The preconfigured first object includes a name and a communication address of the first object. The communication address may include a telephone number, an E-mail address, and an IP address, etc. The first information may be transmitted to the first object based on the communication address when the alarm operation is performed. Moreover, the first information may be content information preedited by the user or video information or audio information prerecorded by the user. The first information may be transmitted to the first object when the alarm operation is performed. The first object and the first information may be stored in a memory 40 of the electronic device or may be directly stored in the first processing component 30. The first processing component 30 may read the above information from the memory 40 to perform the corresponding configuration.

Specifically, the first processing component 30 may receive the physiological feature parameter obtained from the detecting component 10, and may perform the alarm operation when an exception occurs in the physiological feature parameter (the presupposed condition is satisfied). The physiological feature parameter satisfying the presupposed condition includes: the obtained physiological feature parameter falls outside a preset standard range, correspondingly, different physiological features have different preset standard ranges, and different users may have different preset standard ranges. The preset standard range may be a range value generated based on information captured in the user's daily life, or may be a standard range value inputted by the user.

Moreover, the electronic device uses a double password separation system to perform a security control operation.

That is, at least two types of verification information may be included. For example, the verification information may include first verification information and second verification information. When the user inputs the first verification information, the first processing component 30 may perform the normal operating mode of the electronic device based on the first verification information, for example, entering a corresponding program page such as a main interface of device. In an embodiment, when the user inputs the second verification information, the first processing component 30 may perform the alarm operation of the electronic device, i.e., the preconfigured first information may be transmitted to the first object. At this moment, the first processing component 30 also may display prompt information on the electronic device. The prompt information may be, for example, information prompting a password input error. In an embodiment, just like the first verification information, the first processing component 30 may enter the corresponding program interface of device to perform the normal operation of the electronic device. Through the above configuration, the alarm operation may be performed in unobservable cases, and thus the user security may be improved.

Moreover, the first verification information and second verification information in this embodiment of the present disclosure may be the same type of verification information or may be different types of verification information. As shown in FIG. 2, a schematic diagram when the first verification information and the second verification information in this embodiment of the present disclosure are the same type of verification information is shown. The first verification information and the second verification information may be composed of characters. For example, the first verification information is 1234, and the second verification information is 4321. The user may input the second verification information when the alarm operation is performed. In other embodiments of the present disclosure, the first verification information and the second verification information also may be audio verification information, graphic verification information, biological feature information and so on, which are not specified here.

In another embodiment of the present disclosure, the first verification information and the second verification information may be different types of verification information. For example, the first verification information may be fingerprint information, and the second verification information may be character information. In other embodiments, the first verification information and the second verification information respectively may be two types of information of character verification information, biological feature information, audio information, or other verification information. The processing component 30 also may be further configured to turn off the biological feature input module 21 of the input component 20 when the physiological feature parameter received from the detecting component 10 satisfies the presupposed condition, wherein the second verification information is composed of characters or graphs. In an embodiment, the processing component 30 also may be configured to turn off the character input module or the graphic input module when the physiological feature parameter satisfies the presupposed condition. At this moment, the second verification information includes preset biological feature information. That is, when the alarm operation is performed, the first processing component 30 may turn off the input module except the input module of the second verification information, such that the user may input the verification information only by means of the input module corresponding to the second verification information to perform the alarm operation. This configuration may further ensure that the user can input the verification information required to perform the alarm operation, and failure of performing the alarm operation due to misinput of other verification information may be prevented, and thus accuracy of alarm may be further enhanced.

For example, when the first verification information is the fingerprint information, the fingerprint unlocking function may be automatically disenabled in case of abnormal heart rhythm to prevent from entering the normal operating mode due to direct fingerprint unlocking. In this case, the user may select to input a corresponding password based on current environment so as to avoid interference caused by other emotional excitements, thereby preventing the device from making an erroneous determination, and improving alarm accuracy. A double password separation mode is automatically enabled when the heart rate is abnormal if no normal password is set, and the user may perform the operation according to circumstances.

Furthermore, according to the above embodiment, the first processing component 30 also may take the physiological feature parameter detected by the detecting component 10 as a historical parameter and store the historical parameter into the memory 40 in real time, and determine whether the detected physiological feature parameter satisfies the presupposed condition based on the historical parameter. The user's standard physiological feature parameter range in normal circumstances may be generated based on the user's daily physiological feature parameter, and this range is used as a reference to determine whether the physiological feature parameter obtained by the detecting component 10 satisfies the presupposed condition. That is, it is determined whether the physiological feature parameter falls outside the above standard physiological feature parameter range. It is determined that the physiological feature parameter satisfies the presupposed condition if the physiological feature parameter falls outside the standard physiological feature parameter range, otherwise it is determined that the physiological feature parameter does not satisfy the presupposed condition.

For example, if the electronic device is robbed, the detecting component 10 in the electronic device may detect that the user's heart rate is abnormal in the robbery, or even detect heart rates of two persons. At this moment, the electronic device may automatically perform the alarm operation or may perform the alarm operation by means of the wearable component by communicating with the wearable component. When one of the first device and the second device is robbed, the other device may perform detection of the user's physiological feature parameter, such that the other device may perform an alarm based on the received second verification information when the physiological feature parameter is abnormal. In an embodiment, when one of the first device and the second device is robbed, the detecting component in the robbed device may detect the robber's physiological feature parameter, and may perform the alarm operation or may perform the alarm operation by means of the second device when determining that this parameter does not conform to the user's standard physiological feature parameter or is the physiological feature parameter of a second user other than a preset user.

In an embodiment, when a wearable component such as a smart wristband is robbed, the user's heart rate is abnormal, and the wristband may sense an external force and thus automatically turn on the alarm system. At this moment, the wearable component also may communicate with the electronic device and perform the alarm operation by means of the electronic device.

The alarm operation in this embodiment of the present disclosure is described below in detail. In addition to transmitting the preconfigured first information to the first object, the first processing component 30 also may perform a preset operation at a preset time interval, wherein the preset operation includes at least one of:

photographing an image via a photographing device and storing the image, and transmitting the image to the first object;

obtaining audio information via a voice recording device and storing the audio information, and transmitting the audio information to the first object; and obtaining positioning information via a positioning device and storing the positioning information, and transmitting the positioning information to the first object.

That is, the first processing component 30 also may connect to at least one of a photographing device, a recording device and a positioning device of the electronic device, and may store image information obtained by the photographing device, audio information obtained by the recording device and positioning information obtained by the positioning device into the memory, and transmit the obtained information to the first object, such that the first object may learn about the user's current situations and accordingly adopt effective safety precautions.

For example, when the user is coerced to call the user's relatives, because of abnormal heart rate caused by emotional variations, the detecting component 10 may detect that the user's current heart rate parameter satisfies the presupposed condition and enter the alarm mode. At this moment, the user inputs a special password, i.e., the second verification information to start the alarm system. At this moment, the electronic device automatically takes photos and records voices at background, and keeps on transmitting the photos, the recorded voices and the current position, and preset information or voices (for example, I am in danger, please help me) to the designated first object.

In another embodiment, the first processing component 30 also may search for a monitoring apparatus within a preset range based on positioning information obtained by the positioning device, store an identifier of the monitoring apparatus, and transmit the identifier to the first object.

For example, the electronic device may establish a communication connection with an external server to request to obtain the monitoring apparatus within the preset range of the positioning information. Specifically, the first processing component 30 may transmit a first request to the server based on the received second verification information, wherein the first request may include the positioning information obtained by the positioning device. When the server receives the first request, the server may obtain the identifier of the monitoring apparatus within a preset range from the positioning information in the first request, and return the obtained identifier back to the electronic device. The first processing component 30 may store the identifier of the monitoring apparatus returned by the server into the memory, and transmit the identifier of the monitoring apparatus within the preset range to the first object. In this way, the user's security is further improved, and the alarm operation may be performed based on a monitoring video obtained by the monitoring apparatus. In an embodiment, the first processing component 30 also may obtain the corresponding monitoring video based on the monitoring apparatus searched out.

In an embodiment, configuration information of the monitoring apparatus may be stored in the memory of the electronic device. The configuration information may include, for example, location information and corresponding identification information of the monitoring apparatus within a certain regional range. After obtaining the second verification information, the first processing component may search the identifier of the monitoring apparatus within the preset range based on the positioning information obtained by the positioning device, and transmit the identifier to the first object.

Through the above configuration, information on the monitoring apparatus within the preset range may be conveniently obtained, which may conveniently help the user to obtain the corresponding monitoring video and further guarantee security of the user and collection of evidence, etc.

Furthermore, in another embodiment of the present disclosure, when the electronic device establishes a communication connection with the wearable component, wherein the wearable component may include, for example, a smart wristband, smart clothes or the like, the wearable component may be provided with the detecting component 10. Further, the first processing component 30 also may include a first processing module 31 and a second processing module 32, wherein the first processing module 31 and the second processing module 32 may execute the same configuration as the first processing component 30, such that no matter the electronic device or the wearable component in communication connection with the electronic device may perform control of the alarm operation. When one of the electronic device and the wearable component goes wrong or the alarm operation cannot be performed due to restriction of other conditions, the other one may perform the alarm operation, and thus availability of the alarm operation may be further improved.

Here, the electronic device and the wristband may perform data transmission by way of wireless communication connection. The electronic device and the wristband may respectively include a wireless communication module such as a Bluetooth module, a WiFi module, or a near field communication (NFC) module.

Furthermore, the first input component 20 also may receive second information, and the first processing component 30 may stop performing the alarm operation based on the second information. The first input component 20 may receive the second information by receiving preset voice information, preset key information or preset gesture operation information, etc.

In conclusion, according to the alarm control method in this embodiment of the present disclosure, the preset alarm operation may be conveniently and safely performed, and security of the user can be guaranteed.

Those skilled in the art may clearly understand that for convenience and concision of description, reference may be made to corresponding description of the foregoing product embodiments for the electronic device to which the data processing method set forth above is applied, and thus detailed description of the electronic device is omitted herein.

The above embodiments are merely exemplary embodiments of the present disclosure, and are not intended for limiting the present disclosure, and the scope of protection of the present disclosure is limited by the claims. Those skilled in the art may make various modifications or equivalent substitutions on the present disclosure within the essence and the scope of protection of the present disclosure, which shall also be deemed as falling within the scope of protection of the present disclosure.

What is claimed is:

1. An electronic device, comprising:
   a detecting component, configured to obtain a physiological feature parameter of a user;
   a first input component, configured to receive verification information inputted by the user; and
   a first processing component, configured to receive the verification information via the first input component when determining that the physiological feature parameter obtained by the detecting component satisfies a condition, to control the electronic device to perform a normal operating mode when the verification information received by the first input component is first verification information, and to control the electronic device to perform an alarm operation when the verification information received by the first input component is second verification information; wherein the alarm operation at least comprises transmitting first prestored information to a first object.

2. The electronic device according to claim 1, further comprising a second input component;
   wherein the second input component is configured to receive the verification information inputted by the user;
   the electronic device is configured to perform the normal operating mode when the verification information received by the second input component is third verification information; and
   the first processing component is configured to turn off the second input component when determining that the physiological feature parameter obtained by the detecting component satisfies the condition.

3. The electronic device according to claim 2, wherein the first verification information is different from the second verification information and the third verification information, and the second verification information is different from the third verification information.

4. The electronic device according to claim 2, wherein the first verification information is the same as the third verification information, and is different from the second verification information.

5. The electronic device according to claim 2, wherein the first verification information, the second verification information and the third verification information comprise at least one of biological feature information, character information and graphic information.

6. The electronic device according to claim 2, wherein both the first input component and the second input component comprise at least one of: a biological feature input module, a character input module, and a graphic input module; and
   the biological feature input module comprises at least one of a fingerprint input module, an iris input module, and a facial feature input module.

7. The electronic device according to claim 1, wherein the detecting component comprises at least one of a heart rate sensing module, a blood pressure sensing module, and a blood glucose detecting module.

8. The electronic device according to claim 1, further comprising a first device and a second device in a mutual communication connection, wherein
   the detecting component comprises: a first detecting module arranged in the first device, and a second detecting module arranged in the second device; the first detecting module and the second detecting module are configured to obtain the physiological feature parameter of the user;

the first input component comprises: a first input module arranged in the first device, and a second input module arranged in the second device;

the first processing component comprises a first processing module arranged in the first device, and a second processing module arranged in the second device; the first processing module and the second processing module are configured to start the first input component when the physiological feature parameter obtained by the detecting component satisfies the condition; and the first processing component is configured to control the electronic device to perform the normal operating mode when the verification information received by the first input component is first verification information, and perform the alarm operation when the verification information received by the first input component is second verification information.

9. The electronic device according to claim 8, wherein the first device comprises at least one of a mobile phone, a PAD, and a notebook computer; and the second device comprises a wearable device, and the wearable device comprises a smart wristband.

10. The electronic device according to claim 1, wherein the first processing component is further configured to control the electronic device to perform the normal operating mode when performing the alarm operation or after performing the alarm operation.

11. The electronic device according to claim 1, wherein the first processing component being configured to perform the alarm operation comprises: performing an operation at a time interval, the operation comprising at least one of:
   photographing an image via a photographing device and storing the image, and transmitting the image to the first object;
   obtaining audio information via a voice recording device and storing the audio information, and transmitting the audio information to the first object; and
   obtaining positioning information via a positioning device and storing the positioning information, and transmitting the positioning information to the first object.

12. The electronic device according to claim 1, wherein the first processing component is further configured to:
   query a monitoring apparatus within a range based on an obtained positioning information;
   store an identifier of the monitoring apparatus, and transmit the identifier to the first object; and
   obtain a corresponding monitoring video based on the queried monitoring apparatus.

13. The electronic device according to claim 1, further comprising a memory, wherein the first processing component is configured to take the physiological feature parameter detected by the detecting component as a historical parameter and store the historical parameter into the memory in real time, and to determine whether the detected physiological feature parameter satisfies the condition based on the historical parameter.

14. An alarm control method, applied to the electronic device according to claim 1 and comprising:
   detecting the physiological feature parameter of the user;
   receiving inputted verification information via the first input component when determining that the physiological feature parameter satisfies the condition; and
   controlling the electronic device to perform the normal operating mode when the verification information is first verification information, and controlling the electronic device to perform the alarm operation when the verification information is second verification information; wherein the alarm operation at least comprises transmitting first prestored information to the first object.

15. The method according to claim 14, further comprising:
   turning off a second input component when determining that the physiological feature parameter satisfies the condition;
   receiving the verification information via the second input component when the physiological feature parameter does not satisfy the condition; and
   controlling the electronic device to perform the normal operating mode when determining that the verification information received by the second input component is third verification information.

16. The method according to claim 15, wherein the verification information comprises at least one of: biological feature information, character information, and graphic information; and
   the biological feature information comprises at least one of fingerprint information, iris information, and facial feature information.

17. The method according to claim 14, further comprising:
   controlling the electronic device to perform the normal operating mode when performing the alarm operation or after performing the alarm operation.

18. The method according to claim 14, wherein the performing the alarm operation further comprises:
   querying a monitoring apparatus within a range based on an obtained positioning information; and
   storing an identifier of the monitoring apparatus, and transmitting the identifier to the first object.

* * * * *